(12) United States Patent
Mansell (10) Patent No.: US 12,290,528 B2
(45) Date of Patent: May 6, 2025

(54) COMPOSITIONS AND METHODS FOR TREATMENT OF SEPSIS-RELATED DISORDERS

(71) Applicant: John Mansell, Gillette, WY (US)

(72) Inventor: John Mansell, Gillette, WY (US)

( * ) Notice: Subject to any disclaimer, the term of this patent is extended or adjusted under 35 U.S.C. 154(b) by 0 days.

(21) Appl. No.: 18/302,841

(22) Filed: Apr. 19, 2023

(65) Prior Publication Data
US 2023/0285440 A1    Sep. 14, 2023

Related U.S. Application Data

(63) Continuation of application No. 16/647,853, filed as application No. PCT/US2018/052050 on Sep. 20, 2018, now Pat. No. 11,642,365.

(60) Provisional application No. 62/562,060, filed on Sep. 22, 2017.

(51) Int. Cl.
| | | |
|---|---|---|
| C07H 21/02 | (2006.01) |
| A61K 31/713 | (2006.01) |
| A61K 38/00 | (2006.01) |
| A61P 31/00 | (2006.01) |
| C12N 15/113 | (2010.01) |

(52) U.S. Cl.
CPC .......... *A61K 31/713* (2013.01); *A61K 38/005* (2013.01); *A61P 31/00* (2018.01); *C12N 15/1137* (2013.01); *C12N 2310/14* (2013.01); *C12Y 114/13039* (2013.01); *C12Y 304/24086* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 2005/0227935 A1 | 10/2005 | McSwiggen et al. |
| 2009/0036396 A1* | 2/2009 | Chatterton ......... C12N 15/1136 536/24.5 |

FOREIGN PATENT DOCUMENTS

| | | |
|---|---|---|
| KR | 20070103671 A | 10/2007 |
| KR | 20120093306 A | 8/2012 |
| WO | 2003027229 A2 | 4/2003 |
| WO | 2003027229 A3 | 4/2003 |
| WO | 2005120569 A2 | 12/2005 |
| WO | 2005120569 A3 | 12/2005 |
| WO | 2010046889 A1 | 4/2010 |
| WO | 2010127400 A1 | 11/2010 |
| WO | 2011131693 A2 | 10/2011 |
| WO | 2011131693 A3 | 10/2011 |
| WO | 2012064865 A1 | 5/2012 |
| WO | 2015075557 A2 | 5/2015 |

OTHER PUBLICATIONS

Allinson et al. (Eur. J. Biochem. 271, 2539-2547 (2004)).*
Erikson et al. (Critical Care (2017) 21:86, pp. 1-8).*
Powers et al. (JID, 2012, 206, 352-356).*
Elliott et al. (Journal of Molecular and Cellular Cardiology, 62, Jan. 7, 2013).*
Foley, N.M. et al., "Current knowledge and future directions of TLR and NOD signaling in sepsis", Military Medical Research, 2015, vol. 2, issue 1, 10 pages.
Shimada, K. et al., "The NOD/RIP2 Pathway Is Essential for Host Defenses Against Chlamydophila pneumoniae Lung Infection", PLoS Pathogens, 2009, vol. 5, Issue 4 article e1000379, 13 pages.
Rochette et al. (Pharmacology & Therapeutics, 140, 2013, 239-257).
Elbashir et al. (The EMBO Journal, vol. 20, No. 23, pp. 6877-6888, 2001).
Hoque, Azizul M., et al., "Effects of antisense oligonucleotide to INOS on hemodynamic and vascular changes nduced by LPS", American Journal of Physiology Heart and Circulatory Physiology, vol. 275, No. 3, Sep. 1, 1998, pp. H1078-H1083, XP055798360.
Homae KR et al., "Antisense Oligodeoxynucleotide to Inducible Nitric Oxide Synthase Inhibits Nitric Oxide Synthesis in Rat Pulmonary Artery Smooth Muscle Cells in Culture", Surgery, Mosby, Inc., vol. 114, No. 2, Aug. 1, 1993, pp. 272-277, XP000866441.
Korean Patent Office, International Search Report, issued in PCT/US2018/052050, May 16, 2019, 4 pages.
Korean Patent Office, Written Opinion, issued in PCT/US2018/052050, May 16, 2019, 5 pages.
European Patent Office, Supplementary Partial Search Report issued in corresponding EP Application No. 18858850, May 4, 2021, 16 pages.

* cited by examiner

*Primary Examiner* — Amy Rose Hudson
(74) *Attorney, Agent, or Firm* — Barnes & Thornburg LLP; Jerry C. Harris, Jr.

(57) ABSTRACT

A method comprising administering, to a subject in need thereof, an effective amount of a nucleotide effective to disrupt one or more pathways leading to sepsis. The nucleotide may be a nitric oxide disruptor effective to decrease the expression of inducible nitric oxide synthase. The nitric oxide disrupter may comprise a polynucleotide strand exhibiting at least 70% sequence identity to one of Sequence ID No. 1 through Sequence ID No. 47. Additionally or alternatively, the nucleotide may be an α disintegrin and metalloproteinase (ADAM) enzyme inhibitor effective to decrease the expression of ADAM enzyme. The ADAM enzyme inhibitor may comprise a polynucleotide strand exhibiting at least 70% sequence identity to one of Sequence ID No. 48 through Sequence ID No. 56.

7 Claims, 1 Drawing Sheet
Specification includes a Sequence Listing.

COMPOSITIONS AND METHODS FOR TREATMENT OF SEPSIS-RELATED DISORDERS

The content of "SEQUENCE_LISTING_84703_388493_REV.xml" created on Apr. 13, 2023 is the ST.26 (XML format) version of the ASCII text file of the sequence listing named "Sequence_Listing_ST25.txt" which was 8.33 KB in size and was created on Sep. 20, 2018. The "SEQUENCE_LISTING_84703_388493_REV.xml" submitted via the USPTO's "EFS-Web" patent application and document submission system herewith is incorporated herein by reference in its entirety.

CROSS-REFERENCE TO RELATED APPLICATIONS

This application is a continuation of and claims priority to U.S. patent application Ser. No. 16/647,853, FILED Mar. 16, 2020, which is a National Stage Entry of PCT/US2018/052050, filed Sep. 20, 2018, which claims priority to U.S. Provisional Application Ser. No. 62/562,060, filed Sep. 22, 2017, and entitled "Compositions and Methods for Treatment of Sepsis-Related Disorders" which is incorporated herein by reference in its entirety.

TECHNICAL FIELD

The present disclosure relates to compositions and methods for treatment of sepsis and sepsis-related disorders. More particularly, the present disclosure relates to compositions and methods for the inhibition of nitric oxide production by inducible nitric oxide synthase and/or the inhibition of an α disintegrin and metalloproteinase (ADAM) enzyme.

BACKGROUND

The currently accepted immunologic paradigm of sepsis suggests that this disorder is present when the activation of the systemic inflammatory pathways are triggered by infection. The infection initiates an immunologic response (inflammatory cytokine and eicosanoid/coagulation cascade) that propagates independently of the underlying infectious trigger. Septic shock (sepsis with hypotension) has a mortality rate of 40-60%, despite treatment.

Septic patients are in a hyperdynamic state characterized by tachycardia, high cardiac output, low systemic vascular resistance, hypoxemia, oliguria, and lactic acidosis. Following infection there is an increase in the circulating concentrations of catecholamines, cortisol, and glucagon resulting in tachycardia and peripheral vasoconstriction. This phase is followed by a progressive vasodilation associated with high cardiac output and decreased vascular resistance and, in some cases, vasoplegia. Subsequent to this, cardiac failure develops with a progressive fall in cardiac output and marked disturbances in tissue perfusion and oxygenation occur. Hyperglycemia is commonly present and represents the influence of circulating cytokines and glucoregulatory hormones; however, in advanced stages hypoglycemia may occur due to depletion of hepatic glycogen and inhibition of gluconeogenesis. There are also associated marked increases in plasma transaminase activity, urea and bilirubin concentrations, indicative of hepatic and renal injury, while the development of lactic acidosis reflects inadequate tissue perfusion and anaerobic metabolism.

A principal factor in septic shock is the production of the signaling molecule nitric oxide. Nitric oxide (NO), is produced by NO synthase (NOS) which utilizes l-arginine and molecular oxygen as substrates and require the cofactors reduced nicotinamide-adenine-dinucleotide phosphate (NADPH), flavin adenine dinucleotide (FAD), flavin mononucleotide (FMN), and (6R-)5,6,7,8-tetrahydrobiopterin ($BH_4$). Inducible NOS ("iNOS," EC 1.14.13.39, one of three NOS isoforms) generates large amounts of NO that exert cytostatic effects. Specifically, the detrimental fall in blood pressure is predominantly attributable to excess NO production by iNOS induced in the vascular wall.

Recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. These properties make siRNAs potentially useful as therapeutic agents against diseases that are caused by overexpression or mal-expression of genes such as the overexpression of detrimental genes and gene products as a result of sepsis or sepsis-related disorders.

SUMMARY

In some aspects disclosed herein is a method comprising administering, to a subject in need thereof, an effective amount of a nucleotide effective to disrupt one or more pathways leading to sepsis. The nucleotide may be a nitric oxide disruptor effective to decrease the expression of inducible nitric oxide synthase by at least 50%, or by at least 75%. The nitric oxide disrupter may comprise a polynucleotide strand exhibiting at least 70% sequence identity to one of Sequence ID No. 1 through Sequence ID No. 47, or exhibiting at least 80% sequence identity to one of Sequence ID No. 1 through Sequence ID No. 47, or exhibiting at least 90% sequence identity to one of Sequence ID No. 1 through Sequence ID No. 47, or exhibiting at least 95% sequence identity to one of Sequence ID No. 1 through Sequence ID No. 47. Additionally or alternatively, the nucleotide may be an α disintegrin and metalloproteinase (ADAM) enzyme inhibitor effective to decrease the expression of ADAM enzyme by at least 50%, or by at least 75%. The ADAM enzyme inhibitor may comprise a polynucleotide strand exhibiting at least 70% sequence identity to one of Sequence ID No. 48 through Sequence ID No. 56, or exhibiting at least 80% sequence identity to one of Sequence ID No. 48 through Sequence ID No. 56, or exhibiting at least 90% sequence identity to one of Sequence ID No. 48 through Sequence ID No. 56 or exhibiting at least 95% sequence identity to one of Sequence ID No. 48 through Sequence ID No. 56. The subject may be characterized as exhibiting sepsis or a sepsis-related disorder.

In some aspects disclosed herein is a composition comprising a polynucleotide strand exhibiting at least 70% sequence identity to any of SEQ ID NO. 1 through SEQ ID NO 56. The polynucleotide strand may exhibit at least 80% sequence identity to any of SEQ ID NO. 1 through SEQ ID NO 47, or at least 90% sequence identity to any of SEQ ID NO. 1 through SEQ ID NO 47. Additionally or alternatively, the polynucleotide strand exhibits at least 80% sequence identity to any of SEQ ID NO. 48 through SEQ ID NO 56, or at least 90% sequence identity to any of SEQ ID NO. 48 through SEQ ID NO 56. The composition may be formulated for delivery to a subject in need thereof.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Disclosed herein are methods of treating a subject having sepsis or a sepsis-related disorder comprising administering to the subject an oligonucleotide that disrupts one or more of the cellular pathways leading to sepsis (collectively, a "sepsis pathway disrupter").

The term "subject" as used herein, refers to an animal which is the object of treatment, observation, or experiment. By way of example only, a subject may be, but is not limited to, a mammal including, but not limited to, a human. In some instances, the subject is a patient who is undergoing treatment for one or more medical conditions. The terms "treat," "treating," or "treatment," as used herein, include alleviating, abating, or ameliorating a disease or condition, or symptoms thereof; managing a disease or condition, or symptoms thereof; preventing additional symptoms; ameliorating or preventing the underlying metabolic causes of symptoms; inhibiting the disease or condition, e.g., arresting the development of the disease or condition; relieving the disease or condition; causing regression of the disease or condition; relieving a symptom caused by the disease or condition; and/or stopping the symptoms of the disease or condition. Treatment, as used herein, also encompasses any pharmaceutical or medicinal use of the compositions herein.

In an aspect, the subject is administered the compositions disclosed herein in a therapeutically effective amount sufficient for treating, preventing, and/or ameliorating one or more symptoms of a medical condition, disorder, disease, or dysfunction. Hereinafter, for simplicity, the unwanted condition which has been used interchangeably with the terms medical condition, disorder, disease, and dysfunction are collectively referred to as the "medical condition." As used herein, amelioration of the symptoms of the medical condition by administration of a particular composition of the type disclosed herein refers to any lessening, whether lasting or transient, which can be attributed to or associated with administration of compositions of the type disclosed herein. As used herein, a "therapeutically effective amount" means a sufficient amount of the compositions disclosed herein to treat, prevent, and/or ameliorate one or more symptoms of the medical condition. It also may include a safe and tolerable amount of the compositions disclosed herein, as based on industry and/or regulatory standards. As will be understood by the ordinarily skilled artisan, an amount that proves to be a "therapeutically effective amount" in a given instance, for a particular subject, may not be effective for 100% of subjects similarly treated for the medical condition under consideration, even though such dosage is deemed a "therapeutically effective amount" by ordinarily skilled practitioners. The therapeutically effective amount for a particular individual may vary depending on numerous factors such as the nature of the medical condition, severity of the medical condition, subject weight, subject age, and the general health of the subject. It is contemplated that the therapeutically effective amount may be optimized by one or more healthcare professionals in consideration of the particular factors affecting a subject.

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

Figure 1:
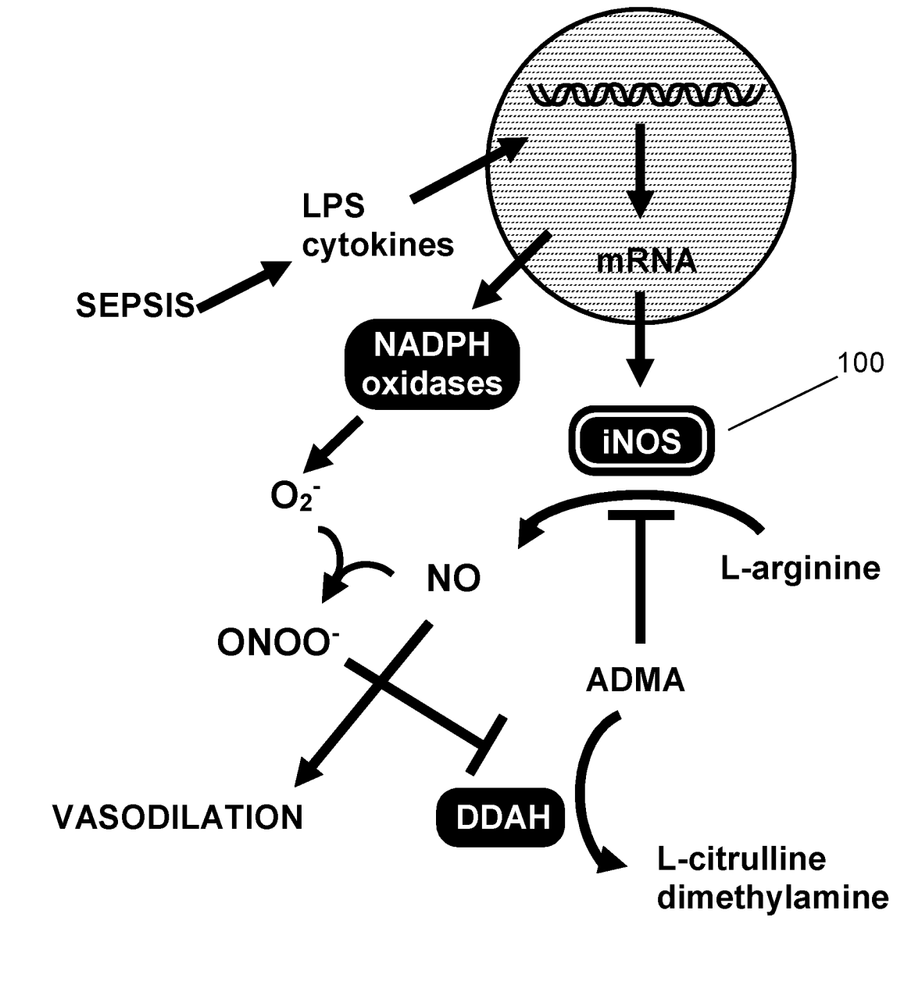
FIG. 1 is a diagram illustrating some of the interactions of various cellular components leading to sepsis.

In an aspect, the method of treatment comprises administering a composition comprising oligonucleotide that may disrupt the production of iNOS. For example, FIG. 1 illustrates a portion of the interactions of various cellular components potentially leading to sepsis. As shown in FIG. 1, administration of a composition effective to disrupt the production of iNOS 100 may disrupt one or more of the cellular pathways leading to sepsis.

In an aspect, gene silencing of iNOS using any of the methodologies or compositions disclosed herein results in a reduction in the circulating concentration of nitric oxide. For example, in some aspects, the sepsis pathway disrupter is a nitric oxide disruptors (NOD).

In an aspect, the compositions disclosed herein result in substantial silencing of the iNOS gene and consequently the reduced production of nitric oxide. As used herein the term "substantial silencing" means that the mRNA of the targeted allele is inhibited and/or degraded by the presence of the introduced NOD, such that expression of the targeted allele is reduced by about 10% to 100% as compared to the level of expression seen when the NOD is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the NOD is not present. As used herein the term "substantially normal activity" means the level of expression of an allele when a NOD has not been introduced. The NODs disclosed herein comprise nucleic acids or nucleotides. The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides. As used herein, the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., .alpha.-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

In an aspect, the NOD is a small interfering RNA (siRNA). Naturally occurring RNAi, a double-stranded RNA (dsRNA) is cleaved by an RNase III/helicase protein, Dicer, into small interfering RNA (siRNA) molecules, a dsRNA of 19-27 nucleotides (nt) with 2-nt overhangs at the 3' ends. siRNAs are incorporated into a multicomponent-ribonuclease called RNA-induced silencing complex (RISC). One strand of siRNA remains associated with RISC and guides the complex toward a cognate RNA that has sequence complementary to the guider ss-siRNA in RISC. This siRNA-directed endonuclease digests the RNA, thereby inactivating it.

As identified in the SEQUENCE LISTING which forms a part of this disclosure, Sequence ID No. 1 through Sequence ID No. 47 (i.e., <210>1 through <210>47) are representative of the sense strand of the NODs described herein. Consequently, the present disclosure contemplates the use of siRNA comprising the sense strands of any of Sequence ID No. 1 through Sequence ID No. 47 and its complementary strand. In an aspect, the siRNAs of the present disclosure comprise the polynucleotides of any of Sequence ID No 1 through Sequence ID No 47 and its perfect complement, alternatively the polynucleotides of any of Sequence ID No 1 through Sequence ID No 47 and a complementary strand. The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present disclosure, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity In an aspect, a NOD comprises a siRNA, a functional variant thereof; or combinations thereof. In some aspects, a functional variant of an siRNA disclosed herein comprises at least 70% sequence identity with any sequence disclosed herein, alternatively at least 75%, alternatively at least 80%, alternatively at least 85%, alternatively at least 90% or alternatively at least 95%.

In general, "identity" refers to an exact nucleotide-to-nucleotide correspondence of two oligonucleotides or polynucleotides sequences. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as Wisconsin Sequence Analysis Package, Version 8 (available from Genetics Computer Group, Madison, Wis.) for example, the BESTFIT, FASTA and GAP programs, which rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Appropriate hybridization conditions may be defined using any suitable methodology.

In some aspects, one or more of the nucleotides present in the siRNA may be modified to achieve one or more user and/or process goals, such as increased stability. Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitromdole, or nebularine. The term "nucleotide" is also meant to include the N3' to P5' phosphoramidate, resulting from the substitution of a ribosyl 3' oxygen with an amine group. Further, the term nucleotide also includes those species that have a detectable label, such as for example a radioactive or fluorescent moiety, or mass label attached to the nucleotide.

Without wishing to be limited by theory, utilization of a NOD of the type disclosed herein would diminish efficient transcription of iNOS mRNA, reduce successful movement of guide strand mRNA to translation and interfere with efficient translation of mRNA which produces iNOS and subsequently nitric oxide.

Additionally or alternatively, in an aspect the method of treatment comprises administering a composition comprising oligonucleotide that may inhibit an α disintegrin and metalloproteinase (ADAM) enzyme, particularly, ADAM 17 (synonyms: CD156b; cSVP; MGC71942; TACE). For example, in some aspects, the sepsis pathway disrupter is an inhibitors of ADAM 17, hereinafter termed A17 inhibitors ("A17I"). A17I are materials which result in a down-regulation or reduction in the activity of ADAM 17. ADAM 17 is a member of the ADAM family of enzymes which are $Zn^{2+}$-dependent, modular cell surface proteins belonging to the adamalysin protein family. They are closely related to other metalloenzymes such as ADAM-TSs (ADAMs with thrombospondin domains), matrix metalloproteinases (MMPs) and snake venom metalloproteinases (SVMP). The structure of ADAMs closely resembles the Class III snake venom metalloenzymes or reprolysines and it forms the basis of the many ADAM enzyme functions. ADAM-17 was discovered in 1997 and described simultaneously by two research groups as the enzyme that releases membrane bound tumor necrosis factor (TNF)-α precursor to a soluble form. This discovery was significant because TNFα is critical in inflammatory processes. ADAM-17 was described as a protein of 824 amino acids (accession number NM_003183), and its gene is located on chromosome 2p25. ADAM-17 is widely expressed in various tissues including the brain, heart, kidney, and skeletal muscle and its expression changes during embryonic development and adult life. ADAM-17 is a multi-domain protein starting with a signal sequence (1-17 aa), followed by a prodomain (18-214 aa), a metalloenzyme or catalytic domain (215-473 aa) with the typical HEXXHXXGXXH (X being any amino acid residue) sequence, a disintegrin domain (474-572 aa), an cysteine-rich domain (603-671 aa), followed by a transmembrane domain (672-694 aa) and a cytoplasmic tail (695-824 aa). The most well-known function of ADAM-17, is to cleave ectodomains of various transmembrane proteins. Proteins with different functions can be processed by ectodomain shedding: EGFR ligands, proinflammatory cytokines like TNFα and its receptor TNFRI, adhesion molecules and the amyloid precursor protein.

The extent of downregulation of ADAM17 or its gene product may be determined using any suitable assay. Suitable assays include without limitation, e.g., examination of protein or mRNA levels using any suitable technique such as dot blots, northern blots, in situ hybridization, ELISA, microarray hybridization, immunoprecipitation, enzyme function, as well as phenotypic assays known to those of skill in the art. To examine the extent of gene silencing, a test sample (e.g., a biological sample from organism of interest expressing the target gene(s) or a sample of cells in culture expressing the target gene(s)) is contacted with a A17I that silences, reduces, or inhibits expression of the target gene(s). Expression of the target gene in the test sample is compared to expression of the target gene in a control sample (e.g., a biological sample from organism of interest expressing the target gene or a sample of cells in culture expressing the target gene) that is not contacted with the A17I. Control samples (i.e., samples expressing the target gene) are assigned a value of 100%. In an aspect, substantial silencing, inhibition, down-regulation or reduction of expression of a target gene is achieved when the value of test the test sample relative to the control sample is about 95%,90%,85%,80%, 75%,70%,65%,60%,55%,50%,45%,40%, 35%, 30%, 25%, 20%, or 10%.

In an aspect the A17I is a microRNA (miRNA, miR). miRs refer to single-stranded RNA molecules that are generally 21-23 nucleotides in length which regulate gene expression. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression through the RNAi pathway.

In an aspect, the A17I is a small interfering RNA (siRNA). Naturally occurring RNAi, a double-stranded RNA (dsRNA) is cleaved by an RNase III/helicase protein, Dicer, into small interfering RNA (siRNA) molecules, a dsRNA of 19-27 nucleotides (nt) with 2-nt overhangs at the 3' ends. The siRNAs may be incorporated into a multicomponent-ribonuclease called RNA-induced silencing complex (RISC). One strand of siRNA remains associated with RISC and guides the complex toward a cognate RNA that has sequence complementary to the guider ss-siRNA in RISC. This siRNA-directed endonuclease digests the RNA, thereby inactivating it. These and other characteristics of RISC, siRNA molecules, and RNAi have been described.

In an aspect, the A17I is an antisense oligonucleotide. Antisense oligonucleotides (ASOs) are synthetic nucleic acids that bind to a complementary target and suppress function of that target. Typically, ASOs are used to reduce or alter expression of RNA targets, particularly messenger RNA (mRNA) or microRNA (miRNA) species. As a general principle, ASOs can suppress gene expression via two different mechanisms of action, including: 1) by steric blocking, wherein the ASO tightly binds the target nucleic acid and inactivates that species, preventing its participation in cellular biology, or 2) by triggering degradation, wherein the ASO binds the target and leads to activation of a cellular nuclease that degrades the targeted nucleic acid species. One class of "target degrading" ASOs are "RNase H active"; formation of heteroduplex nucleic acids by hybridization of the target RNA with a DNA-containing "RNase H active" ASO forms a substrate for the enzyme RNase H. RNase H degrades the RNA portion of the heteroduplex molecule, thereby reducing expression of that species. Degradation of the target RNA releases the ASO, which is not degraded, which is then free to recycle and can bind another RNA target of the same sequence.

In an aspect, an A17I comprises a microRNA, a siRNA, an ASO, an iRNA, an iRNA agent, a shRNA, a functional variant thereof; or combinations thereof. In some aspects, a functional variant of an oligonucleotide disclosed herein comprises at least 70% sequence identity with any sequence disclosed herein, or at least 75%, or at least 80%, or at least 85%, or at least 90%, or at least 95% sequence identity. In general, "identity" refers to an exact nucleotide-to-nucleotide correspondence of two oligonucleotides or polynucleotides sequences. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as Wisconsin Sequence Analysis Package, Version 8 (available from Genetics Computer Group, Madison, Wis.) for example, the BESTFIT, FASTA and GAP programs, which rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

As identified in the SEQUENCE LISTING which forms a part of this disclosure, Sequence ID No. 48 through Sequence ID No. 56 (i.e., <210>48 through <210>56) are representative of the A17Is described herein. In an aspect, the A17I comprises an oligonucleotide having any one of Sequence ID No. 48 through Sequence ID No. 56, alternatively a functional variant thereof. In some aspects, a A17I suitable for use in the present disclosure comprises at least 70% sequence identity with any sequence disclosed herein, alternatively at least 75%, alternatively at least 80%, alternatively at least 85%, alternatively at least 90% or alternatively at least 95%.

In an aspect, the A17I has from about 20% to about a 90% modification or from about a 40% to about 60% modification.

In an aspect, the sepsis pathway disrupters of this disclosure may be included within or comprise a component of a formulation for administration to a subject. The term "formulation" as used herein refers to its generally-accepted meaning in the art, for example, to a composition such as in a pharmaceutically acceptable carrier or diluent, in a form suitable for administration, for example, systemic or local administration, into a cell or subject such as a human. Suitable forms, in part, depend upon the use or the route of entry, for example oral, transdermal, inhalation, or by injection. Such forms should not prevent the formulation from reaching a target cell (i.e., a cell to which the nucleic acid is desirable for delivers). For example, compositions injected into the blood stream should be soluble. Other factors include considerations such as toxicity and forms that prevent the composition or formulation from exerting its effect.

In an aspect, a sepsis pathway disrupter may be formulated for administration to a subject suffering from sepsis or a sepsis-related disorder. The choice of formulation and delivery route for a sepsis pathway disrupter may be driven by patient acceptability, the properties of the sepsis pathway disrupter (such as its solubility), access to a disease location, or effectiveness in dealing with the specific disease.

In an aspect, the sepsis pathway disrupter may be formulated for administration via a peroral route. For example, in an aspect, the sepsis pathway disrupter is delivered via injection for example, following mixing with saline.

In an aspect, the sepsis pathway disrupter may be formulated for administration via pulmonary delivery. Pulmonary delivery may be effected in a variety of ways—via aerosols, metered dose inhaler systems (MDIs), powders (dry powder inhalers, DPIs) and solutions (nebulizers), all of which may contain nanostructures such as liposomes, micelles, nanoparticles and dendrimers. Pulmonary delivery to be a viable option for the delivery of drugs systemically.

In an aspect, the sepsis pathway disrupter may be formulated for administration transdermally. Transdermal delivery avoids problems such as gastrointestinal irritation, metabolism, variations in delivery rates and interference due to the presence of food. It is also suitable for unconscious patients. The technique is generally non-invasive and aesthetically acceptable, and can be used to provide local delivery over several days.

In an aspect, the sepsis pathway disrupter may be formulated for administration parenterally. Trans-tissue and local delivery systems may produce an elevated pharmacological effect, while minimizing systemic, administration-associated toxicity. Trans-tissue delivery systems include: drug-loaded gelatinous gels, which are formed in-situ and adhere to resected tissues, releasing drugs, proteins or gene-encoding adenoviruses; antibody-fixed gelatinous gels (cytokine barrier) that form a barrier, which, on a target tissue could prevent the permeation of cytokines into that tissue; cell-based delivery, which involves a gene-transduced oral mucosal epithelial cell (OMEC)-implanted sheet; device-directed delivery—a rechargeable drug infusion device that can be attached to the resected site.

Once the sepsis pathway disrupters are delivered intracellularly, affinity dynamics with the components of the nuclear, cytoplasmic and ribosomal elements will determine their effectiveness in reducing production and decreasing the intensity of sepsis and sepsis-related disorders.

In an aspect, the sepsis pathway disrupter may be chemically synthesized. Oligonucleotides (e.g., certain modified oligonucleotides or portions of oligonucleotides lacking ribonucleotides) may be synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng. 61, 33-45, and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end.

Alternatively, a sepsis pathway disrupter may be expressed and delivered via a transcript inserted into DNA or RNA vectors. The recombinant vectors can be DNA plasmids or viral vectors. Non-limiting examples of sepsis pathway disrupter-expressing viral vectors can be constructed based on adeno-associated virus, retrovirus, adenovirus, or alphavirus.

In some aspects, pol III-based constructs are used to express the sepsis pathway disrupter. Transcription of the siNA molecule sequences can be driven from a promoter for eukaryotic RNA polymerase I (pol I), RNA polymerase II (pol II), or RNA polymerase III (pol III), (see for example, Thompson, U.S. Pat. Nos. 5,902,880 and 6,146,886). Transcripts from pol II or pol III promoters may be expressed at high levels; the levels of a given pol II promoter in a given cell type depends on the nature of the gene regulatory sequences (enhancers, silencers, etc.) present nearby. Prokaryotic RNA polymerase promoters may also be used, provided that the prokaryotic RNA polymerase enzyme is expressed in the appropriate cells. These exemplary transcription units can be incorporated into a variety of vectors for introduction into mammalian cells, including but not restricted to, plasmid DNA vectors, viral DNA vectors (such as adenovirus or adeno-associated virus vectors). or viral RNA vectors (such as retroviral or alphavirus vectors)

Vectors used to express the sepsis pathway disrupter of the present disclosure can encode one or both strands of a siNA duplex, or a single self-complementary strand that self hybridizes into an siRNA duplex. The nucleic acid sequences encoding the sepsis pathway disrupter of the present disclosure can be operably linked in a manner that allows expression of the sepsis pathway disrupter. In some aspects, the constructs comprising sepsis pathway disrupter may additionally comprise reporter genes (e.g., green fluorescent protein) and selection genes (e.g., for antibiotic resistance).

In one aspect, a carrier system may contain the sepsis pathway disrupter, for example, for delivery. A sepsis pathway disrupter associated with one or more of the delivery vehicles disclosed herein may be referred to as a packaged sepsis pathway disrupter." Non-limiting examples of delivery vehicles suitable for formulation of the nucleic acid molecules of the instant present disclosure include: Lipid Nanoparticles (see for example Semple et al., 2010, Nat Biotechnol., February; 28(2):172-6); P-glycoprotein inhibitors (such as Pluronic P85); biodegradable polymers, such as poly (DL-lactide-coglycolide) microspheres for sustained release delivery (Emerich, D F et al, 1990, Cell Transplant, 8, 47-58); and loaded nanoparticles, such as those made of polybutylcyanoacrylate. Other non-limiting examples of delivery strategies for the nucleic acid molecules of the instant present disclosure include material described in Boado et al., 1998, J. Pharm. Sci., 87, 1308-1315; Tyler et al., 1999, FEBS Lett., 421, 280-284; Partridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. A packaged sepsis pathway disrupter may be further modified to improve properties such as bioavailiability by modification of the packaging (e.g.) using any suitable methodology (e.g., conjugation with a targeting molecule).

In an aspect, a sepsis pathway disrupter may be a component of a kit and may be formulated as a pharmaceutical composition. For example, the sepsis pathway disrupter may be associated with colloidal drug carrier systems such as micellar solutions, vesicle and liquid crystal dispersions, as well as nanoparticle dispersions consisting of small particles of 10-400 nm diameter.

In an aspect, a sepsis pathway disrupter may be associated with a liposome or niosome. Liposomes are a form of vesicles that consist either of many, few or just one phospholipid bilayers. The polar character of the liposomal core enables polar drug molecules to be encapsulated. Amphiphilic and lipophilic molecules are solubilized within the phospholipid bilayer according to their affinity towards the phospholipids. Participation of nonionic surfactants instead of phospholipids in the bilayer formation results in niosomes. siRNA of the type disclosed herein (i.e., sepsis pathway disrupters) can be incorporated without loss of their activity within the hydrophobic domain of vesicle membranes, acting as a size-selective filter, only allowing passive diffusion of small solutes such as ions, nutrients and antibiotics. Thus, sepsis pathway disrupters may be encapsulated in a nanocage and are effectively protected from premature degradation by proteolytic enzymes.

In an aspect, a sepsis pathway disrupter may be associated with a dendrimer. Dendrimers are nanometer-sized, highly branched and monodisperse macromolecules with symmetrical architecture. They consist of a central core, branching units and terminal functional groups. The core together with the internal units, determine the environment of the nanocavities and consequently their solubilizing properties, whereas the external groups the solubility and chemical behavior of these polymers. Targeting effectiveness is affected by attaching targeting ligands at the external surface of dendrimers, while their stability and protection from the Mononuclear Phagocyte System (MPS) is being achieved by functionalization of the dendrimers with polyethylene glycol chains (PEG).

In an aspect, the sepsis pathway disrupter may be associated with a liquid crystal. Liquid crystals combine the properties of both liquid and solid states. They can be made to form different geometries, with alternative polar and non-polar layers (i.e., a lamellar phase) where aqueous drug solutions can be included.

In an aspect, the sepsis pathway disrupter may be associated with a nanoparticle. Nanoparticles (including nanospheres and nanocapsules of size 10-200 nm) are in the solid state and are either amorphous or crystalline. They are able to adsorb and/or encapsulate a drug, thus protecting it against chemical and enzymatic degradation. Nanocapsules are vesicular systems in which the drug is confined to a cavity surrounded by a unique polymer membrane, while nanospheres are matrix systems in which the drug is physically and uniformly dispersed. Nanoparticles as drug carriers can be formed from both biodegradable polymers and non-biodegradable polymers. In recent years, biodegradable polymeric nanoparticles have attracted considerable attention as potential delivery devices in view of their applications in the controlled release of drugs, in targeting particular organs/tissues, as carriers of DNA in gene therapy, and in their ability to deliver proteins, peptides and genes through the peroral route.

In an aspect, the sepsis pathway disrupter may be associated with a hydrogel. Hydrogels are three-dimensional, hydrophilic, polymeric networks capable of imbibing large amounts of water or biological fluids. The networks are composed of homopolymers or copolymers, and are insoluble due to the presence of chemical crosslinks (tie-points, junctions), or physical crosslinks, such as entanglements or crystallites. Hydrogels exhibit a thermodynamic compatibility with water, which allows them to swell in aqueous media. They are used to regulate drug release in reservoir-based, controlled release systems or as carriers in swellable and swelling-controlled release devices. On the forefront of controlled delivery, hydrogels as enviro-intelligent and stimuli-sensitive gel systems modulate release in response to pH, temperature, ionic strength, electric field, or specific analyte concentration differences. In these systems, release can be designed to occur within specific areas of the body (e.g., within a certain pH of the digestive tract) or also via specific sites (adhesive or cell-receptor specific gels via tethered chains from the hydrogel surface). Hydrogels as delivery systems can be very promising materials if combined with the technique of molecular imprinting.

In an aspect, the sepsis pathway disrupter may be a component of a conjugate or complex provided that can impart therapeutic activity by transferring therapeutic compounds across cellular membranes, altering the pharmacokinetics, and/or modulating the localization of nucleic acid molecules of the present disclosure. For example, the conjugate can comprise polyethylene glycol (PEG) can be covalently attached to a sepsis pathway disrupter. The attached PEG can be any molecular weight, for example from about 100 to about 50,000 daltons (Da).

In an aspect, the sepsis pathway disrupter may be a component of a composition or formulation comprising surface-modified liposomes containing poly (ethylene glycol) lipids (PEG-modified, or long-circulating liposomes, or stealth liposomes) and sepsis pathway disrupter. In some aspects, the sepsis pathway disrupter can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In an aspect, the formulation may contain additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

In an aspect, a method of treating a subject having sepsis or a sepsis-related disorder comprises administering to a subject in need thereof a sepsis pathway disrupter of the type disclosed herein. For example, a subject in need thereof may present with sepsis or a sepsis-related disorder. Clinical presentation of sepsis or a sepsis-related disorder may be observed in subjects demonstrating hypotension with low systemic vascular resistance. A trend from normal hemodynamics to a septic state or who are evaluated as being at high risk of clinical presenting with sepsis or a sepsis-related disorder may be administered a continuous infusion with or without a loading or bolus dose of a sepsis pathway disrupter of the type disclosed herein. Administration of a sepsis pathway disrupter comprising a NOD as disclosed herein may result in the reduction or arrest of the production of new endothelial inducible nitric oxide synthase enzymes, resulting in a reduced production of nitric oxide and its resultant vasodilatory effects. Additionally or alternatively, administration of a sepsis pathway disrupter comprising a A17I as disclosed herein may result in a down-regulation or reduction in the activity of ADAM 17. In various aspects, a method of the present disclosure comprises administration of an effective amount of a sepsis pathway disrupter of the type disclosed herein to a subject experiencing sepsis or a sepsis-related disorder may advantageously result in the subject experiencing a normalization of systemic vascular resistance with improved tissue perfusion and oxygenation, reduction of the need for endogenous and administered catecholamine infusions and diminished demands on cardiac output.

What is claimed is:

1. A method comprising administering an oligonucleotide effective to disrupt one or more pathways leading to sepsis to a subject, wherein the oligonucleotide is an α disintegrin and metalloproteinase (ADAMD) enzyme inhibitor, wherein the ADAM enzyme inhibitor is effective to decrease the expression of ADAM enzyme by at least 50%, wherein the ADAM enzyme inhibitor has a length of twenty-one nucleotides, and wherein the ADAM enzyme inhibitor comprises a polynucleotide strand exhibiting at least 70% sequence identity to one of Sequence ID No. 49 through Sequence ID No. 56.

2. The method of claim 1, wherein the oligonucleotide is an α disintegrin and metalloproteinase (ADAM) enzyme inhibitor, wherein the ADAM enzyme inhibitor is effective to decrease the expression of ADAM enzyme by at least 75%.

3. The method of claim 1, wherein the ADAM enzyme inhibitor comprises a polynucleotide strand exhibiting at least 70% sequence identity to one of Sequence ID No. 49 through Sequence ID No. 56.

4. The method of claim 1, wherein the ADAM enzyme inhibitor comprises a polynucleotide strand exhibiting at least 80% sequence identity to one of Sequence ID No. 49 through Sequence ID No. 56.

5. The method of claim 1, wherein the ADAM enzyme inhibitor comprises a polynucleotide strand exhibiting at least 90% sequence identity to one of Sequence ID No. 49 through Sequence ID No. 56.

6. The method of claim 1, wherein the ADAM enzyme inhibitor comprises a polynucleotide strand exhibiting at least 95% sequence identity to one of Sequence ID No. 49 through Sequence ID No. 56.

7. The method of claim 1, wherein the subject is characterized as exhibiting sepsis.

* * * * *

SEQUENCE LISTING

```
Sequence total quantity: 56
SEQ ID NO: 1            moltype = RNA  length = 19
FEATURE                 Location/Qualifiers
source                  1..19
                        mol_type = other RNA
                        organism = synthetic construct
SEQUENCE: 1
gcaactaaat ctagcatta                                                  19

SEQ ID NO: 2            moltype = RNA  length = 19
FEATURE                 Location/Qualifiers
source                  1..19
                        mol_type = other RNA
                        organism = synthetic construct
SEQUENCE: 2
aggaagaggt ggagggtca                                                  19
```

-continued

```
SEQ ID NO: 3                moltype = RNA   length = 19
FEATURE                     Location/Qualifiers
source                      1..19
                            mol_type = other RNA
                            organism = synthetic construct
SEQUENCE: 3
gtgagaagat ggagatcaa                                                    19

SEQ ID NO: 4                moltype = RNA   length = 19
FEATURE                     Location/Qualifiers
source                      1..19
                            mol_type = other RNA
                            organism = synthetic construct
SEQUENCE: 4
caagatagat ggttgatta                                                    19

SEQ ID NO: 5                moltype = RNA   length = 18
FEATURE                     Location/Qualifiers
source                      1..18
                            mol_type = other RNA
                            organism = synthetic construct
SEQUENCE: 5
aggcaaatgg agtgaata                                                     18

SEQ ID NO: 6                moltype = RNA   length = 19
FEATURE                     Location/Qualifiers
source                      1..19
                            mol_type = other RNA
                            organism = synthetic construct
SEQUENCE: 6
ccaaagatat caggagaaa                                                    19

SEQ ID NO: 7                moltype = RNA   length = 19
FEATURE                     Location/Qualifiers
source                      1..19
                            mol_type = other RNA
                            organism = synthetic construct
SEQUENCE: 7
ggacaagtca gatgggcaa                                                    19

SEQ ID NO: 8                moltype = RNA   length = 19
FEATURE                     Location/Qualifiers
source                      1..19
                            mol_type = other RNA
                            organism = synthetic construct
SEQUENCE: 8
tgaaatgacc agagggtga                                                    19

SEQ ID NO: 9                moltype = RNA   length = 19
FEATURE                     Location/Qualifiers
source                      1..19
                            mol_type = other RNA
                            organism = synthetic construct
SEQUENCE: 9
gggagaggct gatcagtta                                                    19

SEQ ID NO: 10               moltype = RNA   length = 19
FEATURE                     Location/Qualifiers
source                      1..19
                            mol_type = other RNA
                            organism = synthetic construct
SEQUENCE: 10
gtgtatttct gtagagcta                                                    19

SEQ ID NO: 11               moltype = RNA   length = 19
FEATURE                     Location/Qualifiers
source                      1..19
                            mol_type = other RNA
                            organism = synthetic construct
SEQUENCE: 11
gttcagagat tgcagtaaa                                                    19

SEQ ID NO: 12               moltype = RNA   length = 19
FEATURE                     Location/Qualifiers
source                      1..19
                            mol_type = other RNA
                            organism = synthetic construct
SEQUENCE: 12
aattatagct cctgacaaa                                                    19
```

```
SEQ ID NO: 13            moltype = RNA   length = 19
FEATURE                  Location/Qualifiers
source                   1..19
                         mol_type = other RNA
                         organism = synthetic construct
SEQUENCE: 13
ctttacagat ggagaatta                                                      19

SEQ ID NO: 14            moltype = RNA   length = 19
FEATURE                  Location/Qualifiers
source                   1..19
                         mol_type = other RNA
                         organism = synthetic construct
SEQUENCE: 14
gagagaagat gtatgtaaa                                                      19

SEQ ID NO: 15            moltype = RNA   length = 19
FEATURE                  Location/Qualifiers
source                   1..19
                         mol_type = other RNA
                         organism = synthetic construct
SEQUENCE: 15
gggcataagt atcagagaa                                                      19

SEQ ID NO: 16            moltype = RNA   length = 19
FEATURE                  Location/Qualifiers
source                   1..19
                         mol_type = other RNA
                         organism = synthetic construct
SEQUENCE: 16
gaactaaaat agaggcata                                                      19

SEQ ID NO: 17            moltype = RNA   length = 19
FEATURE                  Location/Qualifiers
source                   1..19
                         mol_type = other RNA
                         organism = synthetic construct
SEQUENCE: 17
caacagaaga actgagcta                                                      19

SEQ ID NO: 18            moltype = RNA   length = 19
FEATURE                  Location/Qualifiers
source                   1..19
                         mol_type = other RNA
                         organism = synthetic construct
SEQUENCE: 18
aataagagct tctggaatt                                                      19

SEQ ID NO: 19            moltype = RNA   length = 19
FEATURE                  Location/Qualifiers
source                   1..19
                         mol_type = other RNA
                         organism = synthetic construct
SEQUENCE: 19
gctctgaggt cctgacaaa                                                      19

SEQ ID NO: 20            moltype = RNA   length = 19
FEATURE                  Location/Qualifiers
source                   1..19
                         mol_type = other RNA
                         organism = synthetic construct
SEQUENCE: 20
gcatagatgt gacaggaaa                                                      19

SEQ ID NO: 21            moltype = RNA   length = 19
FEATURE                  Location/Qualifiers
source                   1..19
                         mol_type = other RNA
                         organism = synthetic construct
SEQUENCE: 21
agaggaaggt tgaggaaga                                                      19

SEQ ID NO: 22            moltype = RNA   length = 19
FEATURE                  Location/Qualifiers
source                   1..19
                         mol_type = other RNA
                         organism = synthetic construct
SEQUENCE: 22
```

```
gggaaaacgt ttaaagatt                                                    19

SEQ ID NO: 23           moltype = RNA   length = 19
FEATURE                 Location/Qualifiers
source                  1..19
                        mol_type = other RNA
                        organism = synthetic construct SEQUENCE: 23
ggtaagagca tcaaagttt                                                    19

SEQ ID NO: 24           moltype = RNA   length = 19
FEATURE                 Location/Qualifiers
source                  1..19
                        mol_type = other RNA
                        organism = synthetic construct SEQUENCE: 24
ggcataagta tcagagaaa                                                    19

SEQ ID NO: 25           moltype = RNA   length = 19
FEATURE                 Location/Qualifiers
source                  1..19
                        mol_type = other RNA
                        organism = synthetic construct SEQUENCE: 25
ctaaaatgct actggaata                                                    19

SEQ ID NO: 26           moltype = RNA   length = 19
FEATURE                 Location/Qualifiers
source                  1..19
                        mol_type = other RNA
                        organism = synthetic construct SEQUENCE: 26
ccacacaccc taagaatta                                                    19

SEQ ID NO: 27           moltype = RNA   length = 19
FEATURE                 Location/Qualifiers
source                  1..19
                        mol_type = other RNA
                        organism = synthetic construct SEQUENCE: 27
gagaagagtc tatcagtta                                                    19

SEQ ID NO: 28           moltype = RNA   length = 19
FEATURE                 Location/Qualifiers
source                  1..19
                        mol_type = other RNA
                        organism = synthetic construct SEQUENCE: 28
ggatgaaatt gaatggaat                                                    19

SEQ ID NO: 29           moltype = RNA   length = 19
FEATURE                 Location/Qualifiers
source                  1..19
                        mol_type = other RNA
                        organism = synthetic construct SEQUENCE: 29
gagagtgggt aaaggaaat                                                    19

SEQ ID NO: 30           moltype = RNA   length = 19
FEATURE                 Location/Qualifiers
source                  1..19
                        mol_type = other RNA
                        organism = synthetic construct SEQUENCE: 30
ggagtaaaca acagaagaa                                                    19

SEQ ID NO: 31           moltype = RNA   length = 19
FEATURE                 Location/Qualifiers
source                  1..19
                        mol_type = other RNA
                        organism = synthetic construct SEQUENCE: 31
gatggagaat taaggaata                                                    19

SEQ ID NO: 32           moltype = RNA   length = 19
FEATURE                 Location/Qualifiers
source                  1..19
                        mol_type = other RNA
                        organism = synthetic construct
```

```
SEQUENCE: 32
gaaaaggaaa agtgagata                                                    19

SEQ ID NO: 33          moltype = RNA   length = 19
FEATURE                Location/Qualifiers
source                 1..19
                       mol_type = other RNA
                       organism = synthetic construct
SEQUENCE: 33
gctgcaatat ggaaagaaa                                                    19

SEQ ID NO: 34          moltype = RNA   length = 19
FEATURE                Location/Qualifiers
source                 1..19
                       mol_type = other RNA
                       organism = synthetic construct
SEQUENCE: 34
gatagtaact tctgagtca                                                    19

SEQ ID NO: 35          moltype = RNA   length = 19
FEATURE                Location/Qualifiers
source                 1..19
                       mol_type = other RNA
                       organism = synthetic construct
SEQUENCE: 35
ctgagtaatt agaaagcta                                                    19

SEQ ID NO: 36          moltype = RNA   length = 19
FEATURE                Location/Qualifiers
source                 1..19
                       mol_type = other RNA
                       organism = synthetic construct
SEQUENCE: 36
aaggtaagat tgagaggta                                                    19

SEQ ID NO: 37          moltype = RNA   length = 19
FEATURE                Location/Qualifiers
source                 1..19
                       mol_type = other RNA
                       organism = synthetic construct
SEQUENCE: 37
agaatgagag catgagaaa                                                    19

SEQ ID NO: 38          moltype = RNA   length = 19
FEATURE                Location/Qualifiers
source                 1..19
                       mol_type = other RNA
                       organism = synthetic construct
SEQUENCE: 38
cagaaggagc agaagtata                                                    19

SEQ ID NO: 39          moltype = RNA   length = 19
FEATURE                Location/Qualifiers
source                 1..19
                       mol_type = other RNA
                       organism = synthetic construct
SEQUENCE: 39
gggaagatct agtttaaat                                                    19

SEQ ID NO: 40          moltype = RNA   length = 19
FEATURE                Location/Qualifiers
source                 1..19
                       mol_type = other RNA
                       organism = synthetic construct
SEQUENCE: 40
ggaactactt caagcagaa                                                    19

SEQ ID NO: 41          moltype = RNA   length = 19
FEATURE                Location/Qualifiers
source                 1..19
                       mol_type = other RNA
                       organism = synthetic construct
SEQUENCE: 41
aagagaaact ggaggcttt                                                    19

SEQ ID NO: 42          moltype = RNA   length = 19
FEATURE                Location/Qualifiers
source                 1..19
                       mol_type = other RNA
```

-continued

```
                                  organism = synthetic construct
SEQUENCE: 42
ggtaaatgga gaatgttaa                                                                19

SEQ ID NO: 43             moltype = RNA   length = 19
FEATURE                   Location/Qualifiers
source                    1..19
                          mol_type = other RNA
                          organism = synthetic construct
SEQUENCE: 43
tgttattgtt caagagcaa                                                                19

SEQ ID NO: 44             moltype = RNA   length = 19
FEATURE                   Location/Qualifiers
source                    1..19
                          mol_type = other RNA
                          organism = synthetic construct
SEQUENCE: 44
ggttcattct acagagtta                                                                19

SEQ ID NO: 45             moltype = RNA   length = 19
FEATURE                   Location/Qualifiers
source                    1..19
                          mol_type = other RNA
                          organism = synthetic construct
SEQUENCE: 45
agaaaggagg agacagaaa                                                                19

SEQ ID NO: 46             moltype = RNA   length = 19
FEATURE                   Location/Qualifiers
source                    1..19
                          mol_type = other RNA
                          organism = synthetic construct
SEQUENCE: 46
gggctgacac agagaacaa                                                                19

SEQ ID NO: 47             moltype = RNA   length = 19
FEATURE                   Location/Qualifiers
source                    1..19
                          mol_type = other RNA
                          organism = synthetic construct
SEQUENCE: 47
ggatatagaa tgcagctaa                                                                19

SEQ ID NO: 48             moltype = RNA   length = 21
FEATURE                   Location/Qualifiers
source                    1..21
                          mol_type = other RNA
                          organism = synthetic construct
SEQUENCE: 48
gctctcagac tacgatattc t                                                             21

SEQ ID NO: 49             moltype = RNA   length = 21
FEATURE                   Location/Qualifiers
source                    1..21
                          mol_type = other RNA
                          organism = synthetic construct
SEQUENCE: 49
gcagatcatc gcttctacag a                                                             21

SEQ ID NO: 50             moltype = RNA   length = 21
FEATURE                   Location/Qualifiers
source                    1..21
                          mol_type = other RNA
                          organism = synthetic construct
SEQUENCE: 50
gacctggtta caactcatga a                                                             21

SEQ ID NO: 51             moltype = RNA   length = 21
FEATURE                   Location/Qualifiers
source                    1..21
                          mol_type = other RNA
                          organism = synthetic construct
SEQUENCE: 51
gctggagtcc tgtgcatgta a                                                             21

SEQ ID NO: 52             moltype = RNA   length = 21
FEATURE                   Location/Qualifiers
source                    1..21
```

```
                        mol_type = other RNA
                        organism = synthetic construct
SEQUENCE: 52
ggagtcctgt gcatgtaatg a                                             21

SEQ ID NO: 53           moltype = RNA   length = 21
FEATURE                 Location/Qualifiers
source                  1..21
                        mol_type = other RNA
                        organism = synthetic construct
SEQUENCE: 53
gccctatgtc gatgctgaac a                                             21

SEQ ID NO: 54           moltype = RNA   length = 21
FEATURE                 Location/Qualifiers
source                  1..21
                        mol_type = other RNA
                        organism = synthetic construct
SEQUENCE: 54
gaccagctga gcatcaatac t                                             21

SEQ ID NO: 55           moltype = RNA   length = 21
FEATURE                 Location/Qualifiers
source                  1..21
                        mol_type = other RNA
                        organism = synthetic construct
SEQUENCE: 55
gtctctgttt caccccagta a                                             21

SEQ ID NO: 56           moltype = RNA   length = 21
FEATURE                 Location/Qualifiers
source                  1..21
                        mol_type = other RNA
                        organism = synthetic construct
SEQUENCE: 56
gcatcggttc gcattatcaa a                                             21
```